United States Patent [19]
Wenker

[11] Patent Number: 5,972,362
[45] Date of Patent: Oct. 26, 1999

[54] THERAPEUTIC SKIN PREPARATION

[76] Inventor: Naamah T. Wenker, 1610 Smoke Ridge Dr., Colorado Springs, Colo. 80919

[21] Appl. No.: 08/996,538

[22] Filed: Dec. 23, 1997

[51] Int. Cl.⁶ ............................................. A61K 7/48
[52] U.S. Cl. ........................ 424/407; 514/844; 514/847
[58] Field of Search ........................... 424/195.1, 401, 424/DIG. 13; 514/738, 844, 847, 817

[56] References Cited

U.S. PATENT DOCUMENTS

| | | | |
|---|---|---|---|
| 4,822,595 | 4/1989 | Corliss et al. | 424/61 |
| 4,915,973 | 4/1990 | Costa | 424/667 |
| 5,389,279 | 2/1995 | Au et al. | 252/108 |
| 5,738,863 | 4/1998 | Sackin et al. | 424/405 |

*Primary Examiner*—Jose' G. Dees
*Assistant Examiner*—Michael A. Williamson
*Attorney, Agent, or Firm*—Richard W. Hanes

[57] ABSTRACT

Provided is an improved therapeutic skin care preparation that combines traditional moisturizer components including glycerin, aloe vera gel, beeswax, titanium dioxide and fragrance, thickeners including sodium carrageenan, and antiseptic ingredients including tincture of iodine and melaleuca alternifolia. By varying the proportions of these ingredients, skin preparations suitable for particular body areas may be produced. The skin preparation not only performs the traditional functions of treating or preventing the effects on skin of drying, chapping or aging but further serves as a healing agent for minor skin irritation or sores so often associated with such conditions.

2 Claims, No Drawings

THERAPEUTIC SKIN PREPARATION

FIELD OF INVENTION

The present invention relates to skin care preparations and, in particular, to an improved therapeutic skin care preparation.

BACKGROUND OF THE INVENTION

Skin care products, such as lotions and other moisturizers, are well known. The uses of these products are wide-ranging and include relief or prevention of dry or chapped skin and prevention of wrinkles and other problems associated with skin dryness or loss of skin elasticity due to aging. Such products are normally applied directly to dry skin or other areas where moisturizing is desired. However, most, if not all, of these products do not serve as healing agents for skin irritation and minor sores due to dryness or other causes. In fact, such products typically warn potential users against applying the product to such irritated or sore areas, as doing so may only exacerbate the problem.

What is needed in the art is a skin preparation that not only performs the traditional functions of treating or preventing the effects on skin of drying, chapping or aging but further serves as a healing agent for minor skin irritation or sores so often associated with such conditions. The present invention accomplishes these objectives by providing a combination of traditional moisturizer components including glycerin, aloe vera gel, beeswax, additional components including titanium dioxide and fragrance, thickeners including sodium carrageenan, and antiseptic ingredients including tincture of iodine and melaleuca alternifolia. By varying the proportions of these ingredients, skin preparations suitable for particular body areas may be produced.

SUMMARY OF THE INVENTION

The primary aspect of the present invention is to provide a skin preparation that not only performs the traditional functions of treating or preventing the effects on skin of drying, chapping or aging but further serves as a healing agent for minor skin irritation or sores.

Another aspect of the present invention is to provide a method of preparing a skin preparation that not only performs the traditional functions of treating or preventing the effects on skin of drying, chapping or aging but further serves as a healing agent for minor skin irritation or sores.

Additional aspects, advantages and novel features of the invention will be set forth in part in the description which follows, and in part will become apparent to those skilled in the art upon examination of the following or may be learned by practice of the invention. The aspects and advantages of the invention may be realized and attained by means of the instrumentalities and combinations particularly pointed out in the appended claims.

The present invention provides a unique combination of traditional moisturizer components including glycerin, aloe vera gel, beeswax, additional components including titanium dioxide and fragrance, thickeners including sodium carrageenan, and antiseptic ingredients including tincture of iodine and melaleuca alternifolia. By varying the proportions of these ingredients, skin preparations suitable for particular body areas may be produced.

DESCRIPTION OF THE PREFERRED EMBODIMENT

The improved therapeutic skin care preparation of the present invention typically comprises (in percentage by volume):

| | |
|---|---|
| 67–82% | Glycerin |
| 17–19% | Aloe vera gel |
| 0–13% | Beeswax |
| 0.3–2% | Tincture of iodine |
| 0–1.2% | Sodium carrageenan |
| 0.1–1.0% | *Melaleuca alternifolia* |
| 0–0.5% | Titanium Dioxide |
| 0.1–0.2% | Fragrance |

The preparation is produced by thoroughly mixing the glycerin, aloe vera gel, beeswax, tincture of iodine, melaleuca alternifolia, titanium dioxide and fragrance to form a moisturizing mixture. In order to thicken the mixture to the desired consistency, sodium carrageenan is then added and thoroughly mixed into the moisturizing mixture. The resulting skin care preparation is then allowed to sit exposed to room temperature air in order to complete the thickening of the preparation.

Although the present invention has been described with reference to preferred embodiments, numerous modifications and variations can be made and still the result will come within the scope of the invention. No limitation with respect to the specific embodiments disclosed herein is intended or should be inferred.

I claim:

1. An improved therapeutic skin care preparation comprising:

a skin moisturizing agent, wherein the skin moisturizing agent includes by volume of said preparation:
between 67 and 82 percent Glycerin,
between 17 and 19 percent Aloe vera gel,
between 0 and 13 percent Beeswax,
between 0 and 1.2 percent Sodium carrageenan,
between 0 and 0.5 percent Titanium Dioxide, and
between 0.1 and 0.2 percent Fragrance;
between 0.3 and 2% by volume tincture of iodine; and
between 0.1 and 1.0% by volume melaleuca alternifolia.

2. A method for producing an improved therapeutic skin care preparation comprising the steps of:

providing a skin moisturizing agent (in percentage by volume of said preparation):

| | |
|---|---|
| 67–82% | Glycerin |
| 17–19% | Aloe vera gel |
| 0–13% | Beeswax |
| 0–1.2% | Sodium carrageenan |
| 0–0.5% | Titanium Dioxide |
| 0.1–0.2% | Fragrance | adding a predetermined amount of tincture of iodine comprising about 0.3 to about 2% by volume of said preparation; and adding a predetermined amount of melaleuca alternifolia comprising about 0.1 to about 1.0% by volume of said preparation.

\* \* \* \* \*